United States Patent
Stewart (10) Patent No.: US 9,739,597 B2
(45) Date of Patent: **\*Aug. 22, 2017**

(54) METHOD OF AUTHENTICATING A POLYMER FILM BY THICKNESS MEASUREMENT WITH A WHITE LIGHT INTERFEROMETER

(75) Inventor: Robert Laird Stewart, Wigton (GB)

(73) Assignee: INNOVIA FILMS LIMITED, Wigton, Cumbria (GB)

( * ) Notice: Subject to any disclaimer, the term of this patent is extended or adjusted under 35 U.S.C. 154(b) by 833 days.

This patent is subject to a terminal disclaimer.

(21) Appl. No.: 12/937,515

(22) PCT Filed: Apr. 28, 2009

(86) PCT No.: PCT/GB2009/050426
§ 371 (c)(1),
(2), (4) Date: Nov. 11, 2010

(87) PCT Pub. No.: WO2009/133390
PCT Pub. Date: Nov. 5, 2009

(65) Prior Publication Data
US 2011/0043821 A1    Feb. 24, 2011

(30) Foreign Application Priority Data

Apr. 28, 2008 (GB) .................................. 0807668.9

(51) Int. Cl.
G01B 9/02 (2006.01)
G01B 11/06 (2006.01)
G01N 21/23 (2006.01)

(52) U.S. Cl.
CPC ...... *G01B 11/0641* (2013.01); *G01B 11/0675* (2013.01); *G01N 21/23* (2013.01)

(58) Field of Classification Search
CPC .......................... G01B 11/0675; G01B 9/0209
(Continued)

(56) References Cited

U.S. PATENT DOCUMENTS 2,731,621 A * 1/1956 Sontheimer ................... 209/534
3,858,977 A    1/1975 Baird et al.
(Continued)

FOREIGN PATENT DOCUMENTS

GB    2328180    2/1999
JP    2005-254643    9/2005
(Continued)

OTHER PUBLICATIONS

Notification Concerning Transmittal of International Preliminary Report on Patentability and Written Opinion of the International Searching Authority, International Application No. PCT/GB2009/050426.
(Continued)

Primary Examiner — Hwa Lee
(74) Attorney, Agent, or Firm — Ping Wang; Andrews Kurth Kenyon LLP (57) ABSTRACT

A method of authenticating a polymer film comprises measuring the thickness of a layer therein by white light interferometry and/or measuring the birefringence of a layer therein. The method, and devices to carry out the method, may be used in security applications, for example to test for counterfeit bank notes.

12 Claims, 4 Drawing Sheets

(58) Field of Classification Search
USPC .......................................... 356/479, 497, 504
See application file for complete search history.

(56) References Cited

U.S. PATENT DOCUMENTS

| | | | |
|---|---|---|---|
| 4,377,616 | A | 3/1983 | Ashcraft et al. |
| 4,779,898 | A | 10/1988 | Berning et al. |
| 5,737,298 | A | 4/1998 | Suhan |
| 6,045,894 | A | 4/2000 | Jonza et al. |
| 7,057,735 | B2 * | 6/2006 | Jasapara ............... 356/485 |
| 7,148,970 | B2 * | 12/2006 | de Boer ................ 356/497 |
| 2001/0006557 | A1 * | 7/2001 | Mennie et al. ........ 382/135 |
| 2003/0072931 | A1 * | 4/2003 | Hebrink et al. ....... 428/212 |
| 2005/0088663 | A1 * | 4/2005 | De Groot et al. ..... 356/497 |
| 2005/0109984 | A1 | 5/2005 | Potyrailo et al. |
| 2006/0187452 | A1 | 8/2006 | Wang |

FOREIGN PATENT DOCUMENTS

| | | |
|---|---|---|
| WO | 03/033574 A1 | 4/2003 |
| WO | 2005086099 | 9/2005 |
| WO | 2007072426 | 6/2007 |
| WO | 2009133390 | 5/2009 |

OTHER PUBLICATIONS

Search Report Under Section 17(5) of Application No. GB0807668.9 mailed Aug. 8, 2008.
PCT Written Opinion of the International Searching Authority, European Patent Office, Form PCT/ISA/237 of international application No. PCT/GB2009/050426.
Search Report under Section 17(6), UK Intellectual Property Office, application No. GB0807668.9.
Search Report under Section 17(5), UK Intellectual Property Office, Application No. GB0807668.9.

* cited by examiner

Birefringence detector 3

Figure 3

Example: "Genuine" 5 Layer Film

Figure 4

Example "Counterfeit" Five layer film

METHOD OF AUTHENTICATING A POLYMER FILM BY THICKNESS MEASUREMENT WITH A WHITE LIGHT INTERFEROMETER

FIELD

The present invention relates to a method of authenticating a polymer film.

BACKGROUND

Polymer films are increasingly being used as substrates in fields where security, authentication, identification and anti-counterfeiting are important. Polymer-based products in such areas include for example bank notes, important documents (e.g. ID materials such as for example passports and land title, share and educational certificates), films for packaging high-value goods for anti-counterfeiting purposes, and security cards.

Polymer-based secure materials have advantages in terms of security, functionality, durability, cost-effectiveness, cleanliness, processability and environmental considerations. Perhaps the most notable amongst these is the security advantage. Paper-based bank notes, for example, can be relatively easy to copy, and there is lower occurrence of counterfeits in countries with polymer-based bank notes compared to paper-based bank notes. Polymer-based bank notes are also longer-lasting and less-easily torn.

Security materials based on polymer films are amenable to the incorporation of a variety of visible and hidden security features. Since the introduction of the first polymer bank notes approximately 25 years ago, security features have included optically variable devices (OVD), opacification features, printed security features security threads, embossings, transparent windows and diffraction gratings. Aside from complicated security features there is also the more immediate advantage that the high temperatures used in copying machines will often cause melting or distortion of polymer base-material if counterfeiters attempt simply to copy secure materials (e.g. bank notes) using such machines.

A variety of polymers may be used as secure substrates. Amongst these is polypropylene film. The three main methods of manufacturing polypropylene film are the stenter method, the cast method and the bubble method.

In the cast and stenter methods, polymer chips are typically placed in an extruder and heated so that an extrudate is forced out of a slit die onto a chilled roller to form a film (in the case of the cast method) or a thick polymer ribbon (in the case of the stenter method). In the stenter method, the thick polymer ribbon is then reheated and then stretched lengthways (termed the "machine direction") and widthways (termed the "transverse direction") to form a film.

In the bubble method, the polymer is extruded not through a slit die but through an annular die, to form a relatively thick extrudate, in the form of a hollow cylinder or "drainpipe" shape through which air is blown. The annular die is at the top of an apparatus which is typically the equivalent of several storeys high (for example 40 to 50 meters). The extrudate moves downwards and is heated sequentially so that it is expanded to form a bubble. The bubble is then slit into two half-bubbles, each of which may be used individually as "monoweb" films; or alternatively the two halves may be nipped and laminated together to form a double thickness film (or the bubble may be collapsed to form a double thickness film). Typically there are three concentric annuli at the die, so that the hollow cylinder is an extrudate of three layers. For example, there may be a core layer of polypropylene with a terpolymer skin layer on one side and another terpolymer skin layer on the other side. In this case the monoweb would consist of three layers with polypropylene in the middle and the double web would consist of five layers because the layer in the middle would be the same skin layer (terpolymer) of each half-bubble. Many other possible arrangements and components are possible, for example in terms of the number of annuli, type of skin layer, type of core layer, etc.

Thus the bubble method results in a thin film (for example 10 to 100 microns thick) by forming a bubble whereas the stenter method results in a thin film by stretching the material. The bubble method results in homogeneously stretched film which is different to and for some purposes advantageous over stenter film. Biaxially Oriented Polypropylene (BOPP) film is made by the bubble process by Innovia Films Ltd., Wigton, UK. In addition to polypropylene, other polymers (e.g. LLDPE, polypropylene/butylene copolymers) may also be formed as thin films using the bubble process.

It would be desirable to introduce features in a film used as a substrate for security documents, identity documents or value documents and articles which are not readily apparent to a potential unauthorised user or counterfeiter, and which even if identified cannot be readily reproduced. The introduction of such security features may also be applicable to other tokens or articles requiring verification of authentication, such as entrance documents and tickets.

WO 2007/072426 discloses a method of manufacturing a polarization retardant film and to the use of such a film in security applications.

US 2006/0187452 discloses methods for determining the birefringence level of optical material such as polymeric film.

U.S. Pat. No. 5,737,298 discloses a technique for verifying the authenticity of a particular breed of pirated optical discs using a polarimeter.

JP 2005254643 discloses a multilayer transparent film having a blue shift property in which film of two different refractive indices is sequentially laminated.

US 2005/0109984 discloses a method for authenticating that a test polymer is an authenticatable polymer using a thermochromic compound.

WO 2005/086099 discloses a currency genuineness detection system using a plurality of opto-electronic sensors with both transmission and reflectance properties.

DETAILED DESCRIPTION

From a first aspect the present invention provides a method of authenticating a polymer film comprising measuring the thickness of a layer therein by white light interferometry.

Preferably the measurement is made on a core layer of the film.

Transparent thin film materials reflect from both forward and rear surfaces; light reflected from both of these surfaces will differ in path lengths by a distance determined by the thickness of the transparent layer and the angle of incidence of the light. The reflected light waves will therefore undergo phase changes related to the path length differences. A path length difference equal to $[(2n+1)*\lambda/2$ of a beam of light (where n=0, 1, 2, 3 . . . and $\lambda$=wavelength) will cause the returning waves to be completely out of phase and will therefore result in destructive interference, cancelling out any reflected light. A path length difference equal to $n\lambda$ will cause the returning light waves to be completely in phase with one another in a state known as constructive interference, whereby the returning light is twice as intense as before. Path lengths between these two conditions will cause intermediate degrees of intensification or cancelling out of returning light. Interferometry is a series of techniques which utilise the above phenomena to measure distances and thicknesses of materials.

Monochromatic Interferometry uses a single wavelength source to measure a single interfering response. This technique works well in applications such as surface profilometry or in the measurement of thin optical films where the thickness of the substrate is reasonably well known. However, its use as a method of security verification is limited by the small amount of data returned (a single interference pattern) and the possibility that the resulting patterns could be generated by quite different thicknesses (the above formulae illustrate that the same interference can be generated by path lengths of $\lambda 2$, $3\lambda/2$, $5\lambda/2$, $7\lambda/2$ . . . ).

In contrast to monochromatic interferometry, white light interferometry is used in the present invention. The applicant has found that it is most suitable for measuring multiple layered polymer films in security applications. White light interferometry measures the interference pattern generated by a material across a wavelength range defined by the range and resolution of the spectrometer used. A film with an interference path length of any given size will generate interference across the spectral range under analysis; however, the degree of interference will be determined by how in or out of phase the reflected waves of a particular wavelength become. Therefore, the spectrum obtained in a white light interferometer will be composed of a number of fringes of differing sizes, the largest of which will be for those values of n that are simplest to resolve. The thickness of a layer can be reliably determined via a Fourier transform of the data to give the frequency of the fringes. A further advantage of white light interferometry is that the data collected is sufficient to allow for the measurement of multiple interfering layers and the resolution of the individual thickness of those layers with a single measurement.

From a second aspect the present invention provides a method of authenticating a polymer film comprising measuring the birefringence of a core layer therein.

Birefringence, or double refraction, is a property of materials caused by differences in the refractive indices of the material for the two different polarisations, s- and p-. The resulting effect manifests itself as a rotation of the polarisation angle of light being transmitted through the material; the effect is initiated via an interfacial interaction and propagated through the birefringent material; the degree of birefringence observed is a product of the initial interfacial interaction (i.e. the angle of incidence) and the subsequent path length through the material. The birefringence can be observed in a number of ways, as exemplified below.

The present invention allows a film to be securitized as is. The particular inherent characteristics of the film are observed in the present invention, and there is no need to add any further security or identifying features. This identification allows authentication for security purposes and also allows the film's origin to be determined.

The films referred to herein are generally sheet-form materials, and may be provided as individual sheets, or as a web material which may subsequently be processed (by die cutting for example) to provide sheet or article form materials. When referring to "film" in this specification it is intended, unless expressly provided otherwise, to include films in sheet, article or in web form.

The film may comprise a polyolefin film, for example polyethylene, polypropylene, mixtures thereof, and/or other known polyolefins. The polymeric film can be made by any process known in the art, including, but not limited to, cast sheet, cast film, or blown film. The film or sheet may be of mono layer or of multi-layer construction. Preferably the film or sheet is of multi-layer construction with at least one core layer therein. In the case of a mono layer construction the mono-layer is the core layer. In the event that multiple core layers are provided, the measurement of the thickness of a core layer by white light interferometry, or the measurement of the birefringence of a core layer, may be made on just one and/or on more than one of the core layers. The film may be optionally coated, e.g. with opacifer(s). This invention may be particularly applicable to films comprising cavitated or non-cavitated polypropylene films, with a polypropylene core and skin layers with a thickness substantially below that of the core layer and formed for example from co-polymers of ethylene and propylene or terpolymers of propylene, ethylene and butylene. The film may comprise a biaxially orientated polypropylene (BOPP) film, which may be prepared as balanced films using substantially equal machine direction and transverse direction stretch ratios, or can be unbalanced, where the film is significantly more orientated in one direction (MD or TD). Sequential stretching can be used, in which heated rollers effect stretching of the film in the machine direction and a stenter oven is thereafter used to effect stretching in the transverse direction. Alternatively, simultaneous stretching, for example, using the so-called bubble process, or simultaneous draw stenter stretching may be used.

The films used in accordance with the present invention can be of a variety of thicknesses according to the application requirements. For example they can be from about 5 to about 240 μm thick, preferably from about 10 to about 120 μm thick, more preferably from about 12 to about 100 μm thick, and most preferably from about 14 to about 80 μm thick. Plural layers of films in accordance with the invention may be laminated together to form relatively thick substrates for use as, for example, security cards and the like. The thickness of such laminated structures may be considerably higher than the preferred maximum thickness of the unlaminated film, for example 250 μm or even more.

The film may comprise one or more additive materials. Additives may comprise: dyes; pigments, colorants; metallised and/or pseudo metallised coatings (e.g. aluminium); lubricants, anti-oxidants, surface-active agents, stiffening aids, gloss-improvers, prodegradants, UV attenuating materials (e.g. UV light stabilisers); sealability additives; tackifiers, anti-blocking agents, additives to improve ink adhesion and/or printability, cross-linking agents (such as melamine formaldehyde resin); adhesive layer (e.g. a pressure sensitive adhesive); and/or an adhesive release layer (e.g. for use as the backing material in the peel plate method for making labels). Further additives comprise those to reduce coefficient of friction (COF) such as a terpolymer.

Further additives comprise conventional inert particulate additives, preferably having an average particle size of from about 0.2 µm to about 4.5 µm, more preferably from about 0.7 µm to about 3.0 µm. Decreasing the particle size improves the gloss of the film. The amount of additive, preferably spherical, incorporated into the or each layer is desirably in excess of about 0.05%, preferably from about 0.1% to about 0.5%, for example, about 0.15%, by weight. Suitable inert particulate additives may comprise an inorganic or an organic additive, or a mixture of two or more such additives.

Suitable particulate inorganic additives include inorganic fillers such as talc, and particularly metal or metalloid oxides, such as alumina and silica. Solid or hollow, glass or ceramic micro-beads or micro-spheres may also be employed. A suitable organic additive comprises particles, preferably spherical, of an acrylic and/or methacrylic resin comprising a polymer or copolymer of acrylic acid and/or methacrylic acid. Such resins may be cross-linked, for example by the inclusion therein of a cross-linking agent, such as a methylated melamine formaldehyde resin. Promotion of cross-linking may be assisted by the provision of appropriate functional groupings, such as hydroxy, carboxy and amido groupings, in the acrylic and/or methacrylic polymer.

Clarifying agents may be particularly preferred additives for reducing the haze level of an authenticatable film and thereby increasing the signal strength of the film when subjected to white light interferometry, for example. Low haze films may allow the possibility of using detuned white light interferometers to produce a measurable signal with smaller light sources, narrower wavelength ranges (such as emitted by white light LEDs for example) shorter integration times and/or less demanding optical components and sensors.

Accordingly, the invention specifically contemplates the use of a detuned light emitting device and/or a white light LED source in interferometry measurement of a film comprising one or more clarifying agents.

Suitable clarifying agents may include diesteric salts of phosphoric acid, such as sodium 2,2'-methylenebis(4,6,-di-tert-butylphenyl)phosphate; salts of mono- or poly-carboxylic acids, such as sodium benzoate and aluminum t-butylbenzoate; sorbitol derivatives such as dibenzylidenesorbitol or its $C_1$-$C_8$-alkyl-substituted derivatives, such as methyl-, ethyl- or dimethyl-dibenzylidenesorbitol; inorganic additives such as silica, kaolin or talc; or mixtures of two or more thereof. Other suitable clarifying agents, or combinations thereof will be known to the skilled addressee, or with reference to for example the Plastic Additives Handbook, 5th ed.; Zweifel, H., Ed.; Hanser Publ: Munich, 2001.

Some or all of the desired additives listed above may be added together as a composition to coat the sheet of the present invention and/or form a new layer which may itself be coated (i.e. form one of the inner layers of a final multi-layered sheet) and/or may form the outer or surface layer of the sheet. Alternatively some or all of the preceding additives may be added separately and/or incorporated directly into the bulk of the sheet optionally during and/or prior to the sheet formation (e.g. incorporated as part of the original polymer composition by any suitable means for example compounding, blending and/or injection) and thus may or may not form layers or coatings as such.

Such additives may be added to the polymer resin before the film is made, or may be applied to the made film as a coating or other layer. If the additive is added to the resin, the mixing of the additives into the resin is done by mixing it into molten polymer by commonly used techniques such as roll-milling, mixing in a Banbury type mixer, or mixing in an extruder barrel and the like. The mixing time can be shortened by mixing the additives with unheated polymer particles so as to achieve substantially even distribution of the agent in the mass of polymer, thereby reducing the amount of time needed for intensive mixing at molten temperature. The most preferred method is to compound the additives with resin in a twin-screw extruder to form concentrates which are then blended with the resins of the film structure immediately prior to extrusion.

Formation of a film of the invention (optionally oriented and optionally heat-set as described herein) which comprises one or more additional layers and/or coatings is conveniently effected by any of the laminating or coating techniques well known to those skilled in the art.

For example a layer or coating can be applied to another base layer by a coextrusion technique in which the polymeric components of each of the layers are coextruded into intimate contact while each is still molten. Preferably, the coextrusion is effected from a multi-channel annular die such that the molten polymeric components constituting the respective individual layers of the multi-layer film merge at their boundaries within the die to form a single composite structure which is then extruded from a common die orifice in the form of a tubular extrudate.

A film of the invention may also be coated with one or more of the additives described herein using conventional coating techniques from a solution or dispersion of the additive in a suitable solvent or dispersant. An aqueous latex, (for example prepared by polymerising polymer precursors of a polymeric additive) in an aqueous emulsion in the presence of an appropriate emulsifying agent is a preferred medium from which a polymeric additive or coating may be applied.

Coatings and/or layers may be applied to either or both surfaces of the sheet. The or each coating and/or layer may be applied sequentially, simultaneously and/or subsequently to any or all other coatings and/or layers. If a gas-barrier coating of the present invention is applied to only one side of the sheet (which is preferred) other coatings and/or layers may be applied either to the same side of the sheet and/or on the reverse (other) side of the sheet.

Additionally or alternatively further layers can be provided in the film by coextrusion through a multiple-annuli die, to produce for example two, three, four or more layers in the coextrudate exiting the die.

A coating composition may be applied to the treated surface of sheet (such as the polymer film) in any suitable manner such as by gravure printing, roll coating, rod coating, dipping, spraying and/or using a coating bar. Solvents, diluents and adjuvants may also be used in these processes as desired. The excess liquid (e.g. aqueous solution) can be removed by any suitable means such as squeeze rolls, doctor knives and/or air knives. The coating composition will ordinarily be applied in such an amount that there will be deposited following drying, a smooth, evenly distributed layer having a thickness of from about 0.02 to about 10 µm, preferably from about 1 to about 5 µm. In general, the thickness of the applied coating is such that it is sufficient to impart the desired characteristics to the substrate sheet. Once applied to the sheet a coating may be subsequently dried by hot air, radiant heat or by any other suitable means to provide a sheet of the present invention with the properties desired.

It would also be possible to use combinations of more than one of the above methods of applying additives and/or components thereof to a film. For example one or more additives may be incorporated into the resin prior to making the film and the one or more other additives may be coated onto the film surface.

In a multi-layer film in accordance with the invention having at least a substrate layer and a skin layer, the skin layer is preferably ink printable. The skin layer has a thickness of from about 0.05 µm to about 2 µm, preferably from about 0.1 µm to about 1.5 µm, more preferably from about 0.2 µm to about 1.25 µm, most preferably from about 0.3 µm to about 0.9 µm.

The film may have at least one region thereon having reduced opacity compared to the surrounding film. The opacity of the film may be at least partially provided by the presence in the film of voided (or cavitated) regions. Such voided regions may for example be created by providing in the film at least one voiding agent. The production of voided films is of course well known, and any suitable voiding agent may be used here. Voiding agents are generally particulate materials and may be selected from organic, inorganic or polymeric materials. U.S. Pat. No. 4,377,616 of Mobil Oil Corporation describes a number of these. Voiding agents may be substantially spherical particulate in nature, or may have a higher aspect ratio. For example, the voiding agents described in WO-A-03/033574 may be used.

The opacity of the film may be supplemented with further materials which are not voiding agents, but are opacifying agents. Inorganic fillers such as $TiO_2$ may be mentioned in this connection.

The invention is particularly useful where the film is a film made by the bubble process. The bubble process results in films which have balanced orientation, well-defined and uniform thicknesses and other properties (high tensile strength, low elongation, high gloss and clarity, good puncture and flex-crack resistance, resistance to oils and greases, good water-impermeability) which define a "signature" of the film which indicate that it has been prepared by the bubble process.

Previous attempts to securitize film have included the incorporation of one or more taggants into the film in low concentrations, in an attempt to identify the film by detecting a stimulation response. However, the incorporation of taggants adds cost and complexity, and can interfere with other additives. The present invention allows the assessment and analysis of the information which is inherently and already written into the structure of the film. It is preferable that the identification of the present invention includes identification of a core layer rather than a surface layer, thereby enhancing security by authenticating a layer which is enveloped within the film to the extent that tampering with or manipulation of such layer would be very burdensome and difficult.

In order to differentiate between films (e.g. BOPP films and others) the overall thickness of the film, as well as the thickness of individual layers, for example a laminating layer, may be measured. This allows determination of particular characteristics which are dependent on particular processes, for example a particular bubble process. Additionally, or alternatively, the unique birefringent signature of the film may be assessed and used to determine whether the film was made by a particular process and accordingly whether it is, for example, a genuine bank note or counterfeit. Birefringence depends on the anisotropy of the material and films made by bubble process have different anisotropies and hence different birefringent properties to films made by other processes. Furthermore the precise conditions used in the bubble process will affect the birefringent signature.

Thus the present invention recognises that, rather than needing to add security or identification features, the inherent properties of films made by particular processes, such as the bubble process, are unique and act as a signature.

The authentication processes of the present application, and the devices used for such processes, are generally applicable to a range of polymer film materials, and can be tailored to specific substrates and thicknesses by criteria known in the art. As regards authentication by thickness measurement using white light interferometry, a spectrometer's wavelength range is determined by the line spacing of the spectrometer grating, the length of the detector array and the focal length of the spectrometer optics. The thickness range that can be measured is relative to the size of the spectral range used. In the present invention it is preferred to measure thicknesses of between 0.5 and 100 µm, which corresponds to a spectral range of around 500-1000 nm. Depending on the kind of device used, the desirability of a large spectral range can be balanced against other factors, particularly in small devices. The factors that ideally require balancing in a small device include the spectral range, the spectral resolution and the slit width; these factors determine the thickness range possible, the ability to resolve thin layers and the time taken to obtain a response. In a small device, a large spectral range can be offset by the use of narrower slits so as to obtain satisfactory resolution, sufficient sensitivity and acceptable measuring times. According to the invention, devices may be provided which are specific for authentication of a particular defined thickness.

The detection time of the spectrometer is determined by the minimum amount of time needed to saturate the detector array in the spectrometer. Consequently, the brighter the light, the quicker the saturation. However, the desirability of quick detection times must be balanced by the need to avoid heat damage to the film being authenticated. The use of a pulsed light source, such as a short pulsed xenon white flash lamp can mitigate this problem.

Accordingly, one aspect of the present invention involves the use of a pulsed light source in measurement.

From a further aspect the present invention provides a detection unit which is designed to carry out the method of the present invention. Such a detection unit is tailored to recognise the characteristics of the specific signature of a secure polymer-based material. The detection unit may be used to check the authenticity of the materials; for example in banks, ATMs or note readers used by cashiers.

From a further aspect the present invention provides the use of interferometry and/or birefringence measurement in determining the authenticity of a polymer film-based secure item.

Interferometry relies on optical interference between rays which are reflected from the various surfaces within a film. The interference gives a measure of the optical path length between the surfaces and therefore the film (or layer) thickness. The homogeneity of the boundaries between the layers also affects the measurement. The reflection occurs where the layers have different refractive indices.

The interferometry used in the present invention is white light interferometry because monochromatic interferometry is not sufficiently distinguishing.

Typically a narrow light beam is directed into the material to be measured, and the detector detects the light reflected from the boundaries between the layers. A series of peaks are obtained in an interferogram, showing the location of the corresponding layers. Thus it is possible quickly to inspect multilayer films and webs, without needing to contact or destructively analyse the materials.

The orientation in polymers not only affects properties (mechanical, optical, barrier, and others) but also affects the birefringence due to anisotropy in the refractive indices. Birefringence is the separation of light into two rays caused by such anisotropy and is clearly a function of the process of preparation of the film. For example, BOPP films produced by the bubble process have a particular anisotropic character due to the uniform stretching.

The film is preferably a collapsed bubble film, i.e. contains two half-bubbles laminated together. The lamination layer is preferably a terpolymer.

Some aspects of the invention will now be described by way of example in non-limiting detail by reference to FIGS. 1 to 3 which show components of apparatus for different methods of observing birefringence according to the present invention.

Figure 1:
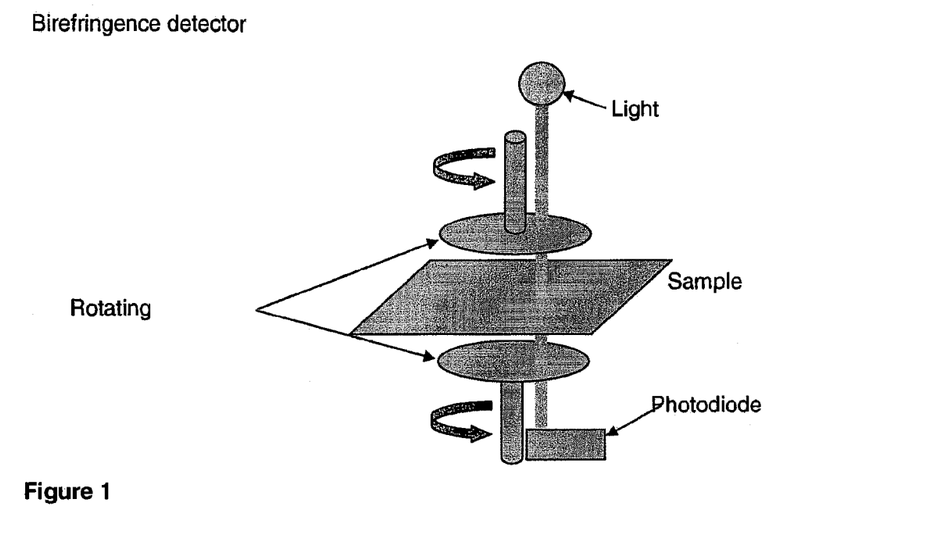
FIG. 1 shows observation of birefringence with crossed polarizers.

With reference to FIG. 1, a first method of observing birefringence is via the use of crossed polarisers. Linear polarisers allow one type of either s- or p-polarised light to pass through them, so that when a second linear polariser is presented and twisted 90° relative to the first, the remaining light made from a single polarised type is filtered out; this technique is referred to as using cross polarisers. Birefringent materials effectively rotate the axis of polarisation and so, when placed between two crossed polarisers will affect how much light is permitted to pass through them. Rotating the birefringent material whilst between the crossed polarisers causes the intensity of light to vary as the angles of birefringence alters. Thin polymer films operate on the first order of birefringence and will tend to rotate light between 0 and 90°; a fully birefringent material will vary from no enhancement in transmission between the polarisers to eliminating the effect of the first polariser by rotating light to pass through the second. This behaviour forms the basis of one method of measuring the birefringence of the films; the sample is typically placed between two motorised cross polarising filters which then rotate through 360° whilst maintaining the same rotationary configuration with respect to one another, light passes from a source through the filter/sample/filter and its intensity is measured using a photodiode. The intensity measured will follow two 180° cycles the maximum and minimum values of which will be related to the birefringence of that film.

Figure 2:
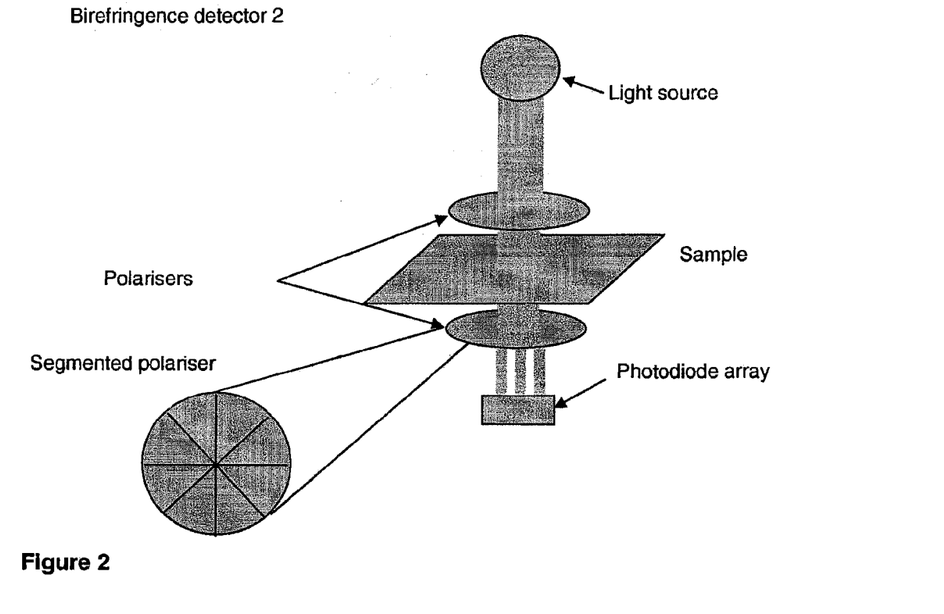
FIG. 2 shows measurement of birefringence with two circular-shaped linear polarising filters.

With reference to FIG. 2, a second method for the measurement of birefringence is to use two circular-shaped linear polarising filters that are composed of sectors of material, each having its own polarisation angle which is related to the angular position of the sector on the circular optic. If two of these optics are differentiated by their s- and p-orientations, then the combination of both will act as cross polarisers for each sector. A single light source can be used to illuminate a sample placed between two such polarisers and the transmitted light from each sector can be fed into an optical fibre which in turn has the intensity transmitted measured using a photodiode. In this way, the birefringent behaviour of the film can be measured in a single measurement without rotating the polarisers—the resolution of such a measurement will depend on the angular size of each of the sectors—for example sectors as large as 20° would give eighteen measurements and would be more than sufficient for the finding of the maximal and the minimal transmissivities.

Figure 3:
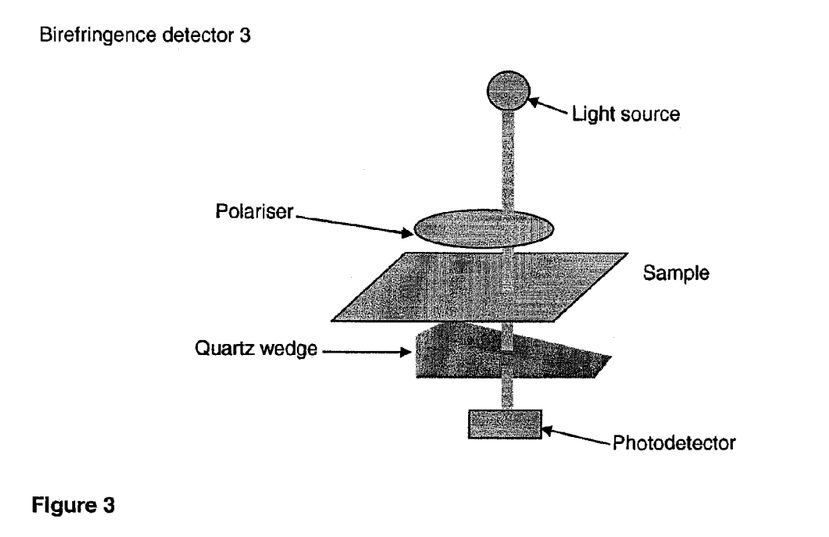
FIG. 3 shows measurement of birefringence with a quartz wedge.

With reference to FIG. 3, a third method for the measurement of the birefringence is the use of a quartz wedge. In this instance, the birefringent material is placed between a polarising filter and a calibrated quartz wedge whilst light is shone through towards an inspection system that measures the positions of fringes on the wedge.

To differentiate between the designated genuine film and others, two methods have been employed in combination that allow the user to eliminate other types of film, i.e. designated counterfeit films:

1. White light Interferometry: measuring the interference pattern generated by layers of a substrate across the visible spectrum supplies the user with the thickness of the layers within a substrate, knowledge of these layers eliminates thinner films, films that have been laminated together (post-process lamination produces much thicker laminating layers) and films of the correct thickness with the wrong layer-by-layer composition. This eliminates cast films (due to thicknesses) and limits severely the choice of BOPP films that the counterfeiter could use.

2. Birefringence: BOPP film made by the stenter process is oriented more in the transverse direction than the machine direction, and so is considerably more birefringent than BOPP films made by the double bubble process. Birefringence can be controlled precisely using the double bubble process and so can provide a unique signature that can eliminate yet more films.

The combination of both tests may also eliminate non-PP films due to thickness, orientation, or co-extrusion limitations.

A protocol was designed in which varying levels of security were assigned (Level 1 being the least secure; Level 6 being the most secure) to methods of determining whether a material contains a film of approximately x micron thickness prepared by collapsing a bubble, each half of which is approximately x/2 microns thick and contains BOPP as core layer and terpolymer as skin layers (the two internal skin layers then resulting in a lamination layer)

Level 1: differentiating between a real and a false product based on thickness differences.

Level 2: differentiating between birefringent and non-birefringent film (i.e. stenter or not).

Level 3: differentiating between film structures (i.e. is this film made from two laminated halves of x/2 micron thickness or not).

Level 4: differentiating between non-birefringent non-bubble films made from two laminated x/2 µm halves and a bubble film.

Level 5: differentiating between bubble films that have been subjected to collapsed bubble lamination, and ones that have been laminated afterwards on a separate process—there will be differences in thickness and birefringence).

Level 6: differentiating between x micron collapsed bubble films produced by one particular bubble process as opposed to a different bubble process.

Detection to any level indicates success—level 1 eliminates 99% of available commercial films; level 2 detection removes the most common films which are similar to bubble-prepared BOPP. Level 4 was regarded as an acceptable level of success; however, at present the detector operates at level 5 and so is regarded as safe from anything apart from an unrealistically determined attempt (i.e. setting up a double bubble process—even then, it might not fool the detector).

The above scale does not suggest that counterfeiting the film is impossible—there are non-standard and as yet unknown methods of achieving a similarly structured film. However, to counterfeit the film would take a considerable amount of expertise on the part of the counterfeiter.

Actual counterfeit film is more likely to be bought rather than made by the counterfeiter. There are several sources that can be broken into three main groupings:

1. Cast or blown films—cast films are made by extruding polymer through a die onto a chilled roller. Blown films are made by extruding a polymer through a circular die and inflating a bubble in the semi-molten state. Cast films & blown films are typically either non or slightly oriented and so have inferior dimensional stability (i.e. they can easily be stretched), poorer optics and thickness control.

2. Mono oriented films—mono oriented films are made by extruding through a die and stretching in the machine direction. Mono oriented films are highly oriented, they have poorer optics and poor transverse direction dimensional stability.

3. Biaxially oriented films—biaxially oriented films are commercially available from Innovia Films Limited and from a number of other suppliers. Commercial grades of BOPP from many suppliers are generally made by the stenter process where PP is extruded through a slot die onto a chill roller, stretched in the machine direction over heated rollers and stretched in the transverse direction in a tenter frame. These films are anisotropic in nature unlike BOPP made by the double bubble process, which is stretch oriented evenly in all directions. Perhaps the greatest counterfeiting threat lies in the lamination together of thinner films to imitate thicker films, which is why the Example which follows was selected, to demonstrate the capability of the inventive method to distinguish between these scenarios.

EXAMPLES 1. 5 Layer (Genuine) Film

Figure 4:
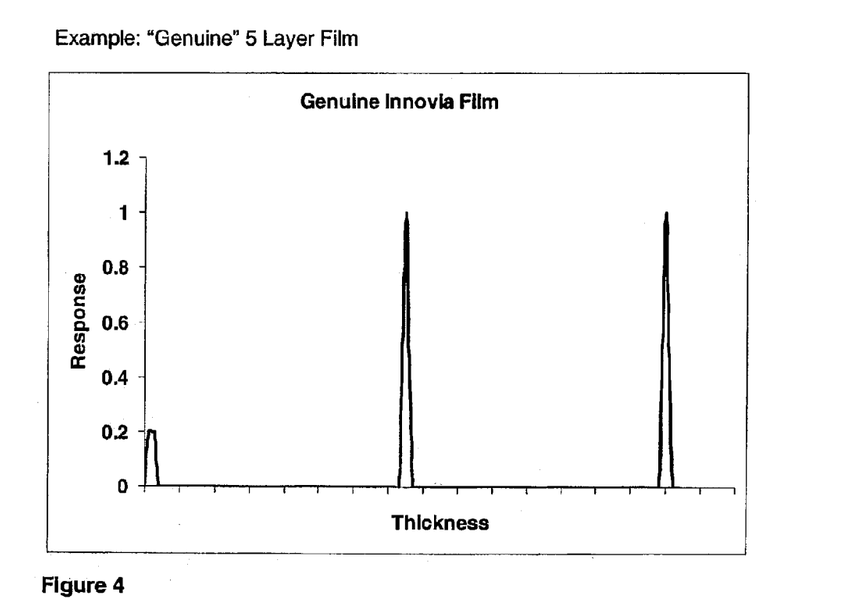
FIG. 4 shows an interferogram of an exemplary "genuine" film.

A five layer film was made using the so-called double bubble process. Molten polymer from three extruders (a large core and two smaller skin extruders) was extruded through an annular die to produce a 1-2 mm thick tube of polypropylene. This tube was then reheated and simultaneously stretched in the transverse and machine directions by a combination of pulling the film in the machine direction and blowing it into a bubble to stretch in the transverse direction. The resulting film had been stretched by 8x8 to produce film of between 20 and 50 µm in thickness. The bubble can either be cut and pulled into two halves (to produce a three layer film) or it can be collapsed and laminated together to produce thick, five layered film of between 50 and 100 µm in thickness. In this Example, a 5 layer film was prepared, and the film was then annealed via reheating and rolled up into reels. The five layers consisted of two outer skin layers (<0.5 µm), two main core areas (20-55 µm) and a single laminating layer holding the two core layers together (<1 µm). From this sample the overall thickness, the thickness of each layer and the birefringence were obtained. The interferogram of the resulting film structure (designated "genuine") is shown in FIG. 4.

2. 5 Layer (Counterfeit) Film

Figure 5:
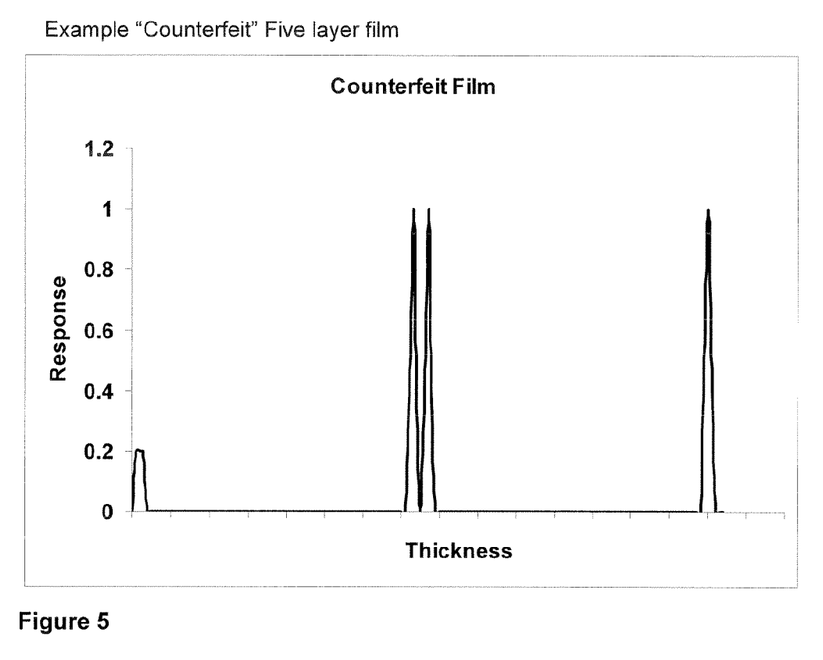
FIG. 5 shows an interferogram of a hypothetical "counterfeit" film manufactured from the designated genuine film by laminating together two webs of the "genuine" film of FIG. 4.
Figure 6:
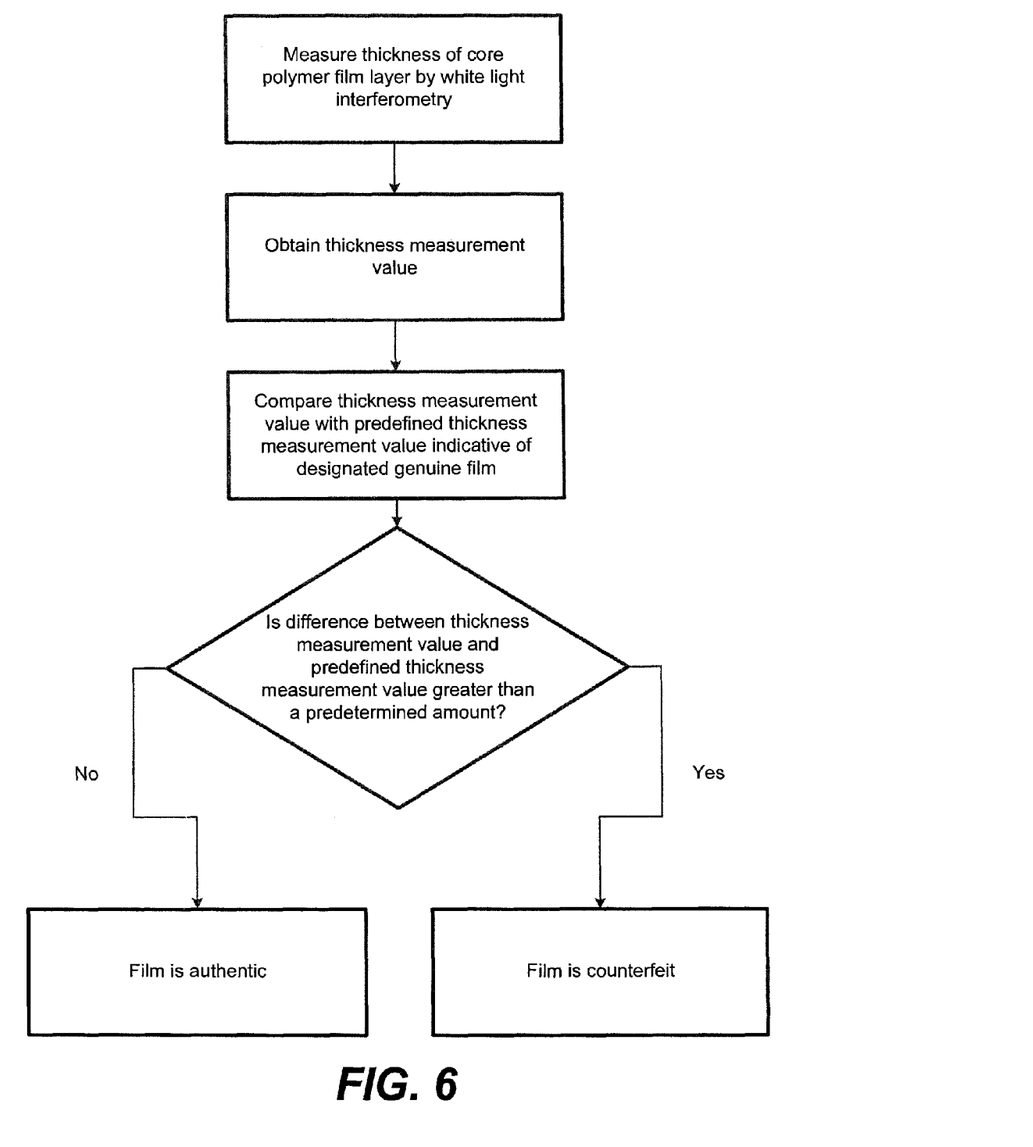
FIG. 6 is a flow chart depicting the measurement of polymer film layer thickness by white light interferometry.

A hypothetical counterfeit film was manufactured from the designated genuine film by laminating together two webs of the "genuine" film. The interferogram of the resulting film structure (designated "counterfeit") is shown in FIG. 5, and shown to be different than the genuine film by the process shown in FIG. 6.

The invention claimed is:

1. A method of authenticating an object comprising a multilayer polymer film comprising a layer of biaxially oriented polypropylene (BOPP), wherein the method comprises the steps of:
    measuring the thickness of a core layer of said multilayer polymer film in the object by white light interferometry and obtaining a thickness measurement value therefrom;
    comparing the thickness measurement value obtained in said measurement step with a predefined thickness value indicative of a genuine object comprising the film; and
    authenticating the object by determining if said polymer film is equivalent or non-equivalent to a polymer film in a genuine object based upon the extent to which the comparison of the thickness measurement value obtained in said measuring step and the predefined thickness value is indicative of a genuine object comprising the film,
    wherein the film is made by a bubble or stenter process.

2. The method according to claim 1, wherein measurement is carried out on more than one layer.

3. The method according to claim 1, wherein measurement is carried out using a pulsed light source.

4. The method according to claim 1, wherein measurement is carried out using a detuned light source.

5. The method according to claim 1, wherein measurement is carried out using an LED light source.

6. The method according to claim 1, wherein the film comprises at least one clarifying agent.

7. The method according to claim 1, wherein the film is a monoweb of three or more polymeric layers.

8. The method according to claim 1, wherein the film is a double web of five or more polymeric layers.

9. The method of claim 1, wherein the object containing the polymer film is:
    a bank note;
    a governmental document;
    a non-governmental document;
    an identity document;
    a passport;
    a security thread;
    an Optical Variable Device (OVD); or
    a wrapper of or an attachment to an item.

10. The method of claim 1, additionally comprising measuring the birefringence of a layer therein.

11. The method according to claim 1, wherein the multilayer polymer film in the genuine object is prepared by a double bubble process producing a five layer film and an interferogram of the polymer film is obtained to determine whether the object is genuine.

12. The method according to claim 1, wherein the object is a bank note.

* * * * *